United States Patent [19]

Ouchi et al.

[11] Patent Number: 5,741,214
[45] Date of Patent: Apr. 21, 1998

[54] ACCESSORY PATHWAY DETECTING/ CAUTERIZING APPARATUS

[75] Inventors: Teruhiko Ouchi; Kunimasa Katayama, both of Nakai-machi, Japan

[73] Assignee: Terumo Kabushiki Kaisha, Tokyo, Japan

[21] Appl. No.: 358,319

[22] Filed: Dec. 19, 1994

[30] Foreign Application Priority Data

Dec. 20, 1993  [JP]  Japan .................................. 5-319705

[51] Int. Cl.$^6$ .......................... A61B 5/042; A61B 17/39; A61N 1/05
[52] U.S. Cl. .......................... 600/374; 600/381; 600/509; 600/547; 606/41; 606/49; 607/122
[58] Field of Search .................................. 128/642, 734, 128/696; 606/41, 49; 607/122, 99, 2; 600/374, 381, 509, 547

[56] References Cited

U.S. PATENT DOCUMENTS

| | | | |
|---|---|---|---|
| 5,341,807 | 8/1994 | Nardella | 128/642 |
| 5,433,198 | 7/1995 | Desai | 128/642 |
| 5,447,529 | 9/1995 | Marchlinski | 128/642 |
| 5,462,545 | 10/1995 | Wang et al. | 128/642 |
| 5,476,495 | 12/1995 | Kordis et al. | 128/642 |
| 5,487,385 | 1/1996 | Avitall | 128/642 |
| 5,524,619 | 6/1996 | Ouchi et al. | 128/642 |
| 5,549,108 | 8/1996 | Edwards et al. | 128/642 |
| 5,549,109 | 8/1996 | Samson et al. | 128/642 |

FOREIGN PATENT DOCUMENTS

| | | |
|---|---|---|
| 0 499 491 | 8/1992 | European Pat. Off. . |
| 62-8174 | 2/1987 | Japan . |

*Primary Examiner*—Lee S. Cohen
*Attorney, Agent, or Firm*—Burns, Doane, Swecker & Mathis, LLP

[57] ABSTRACT

An accessory pathway detecting apparatus measures action potentials from first and second electrode leads, and outputs the obtained action potentials, as potential maps, to a CRT or a printer such that the action potentials can be displayed in the form of a list. An ablation catheter is inserted and located at a preexcitation portion obtained from the display, and the impedance between each of the electrodes of the first and second electrode leads and the electrode of the ablation catheter is measured by an impedance measuring circuit. A point where the lowest impedance is measured is regarded as an accessory pathway portion. The ablation catheter is fixed at this point.

39 Claims, 13 Drawing Sheets

ACCESSORY PATHWAY DETECTING/CAUTERIZING APPARATUS

BACKGROUND OF THE INVENTION

The present invention relates to an accessory pathway detecting apparatus for detecting the accessory pathway in the heart in performing a surgical treatment for a tachycardia arrhythmia such as the Wolf-Parkinson-White syndrome or paroxysmal supraventricular tachycardia.

With the recent advances in electrophysiological test techniques for the heart, medical treatments for arrhythmias have been greatly improved. For example, instead of excision of an accessory pathway portion by conventional open heart surgery, a non-open heart surgery method, which impose less burden on a patient, has been employed. In this method, catheter ablation is performed as follows. An ablation catheter is percutaneously inserted into the heart so as to cauterize an accessory pathway portion by irradiating energy on the accessory pathway portion.

Since tachycardia arrhythmias occur owing to the presence of an accessory pathway other than a normal stimulus conduction pathway in the heart, these treatments are performed by excising or intercepting the accessory pathway by means of cauterization or the like. For this reason, in performing a treatment by means of catheter ablation, the position of an accessory pathway must be specified before cauterization. In a conventional electrophysiological test method, a catheter electrode is inserted into a blood vessel around an atrioventricular annulus in which the accessory pathway exists, an electrical stimulus is applied in the ventricle, and the conduction time of the stimulus is measured. The position of the catheter electrode is sequentially shifted to measure stimulus conduction times at a plurality of portions, and a potential map is manually formed on the basis of this measurement result. A portion exhibiting an abnormal stimulus conduction time is specified as the accessory pathway portion on the basis of this potential map.

When the accessory pathway portion is confirmed upon formation of the potential map, the ablation catheter is guided to a position near the accessory pathway portion (portion to be cauterized) under X-ray fluoroscopy to conduct the above electrophysiological test again by using an electrode mounted on the ablation catheter. With this operation, the accurate position of the accessory pathway portion is specified, and the ablation catheter is fixed thereat.

In the above conventional method, the operator conducts tests while checking the position of the catheter electrode under X-ray fluoroscopy. Tests at a left cardiac mitral annulus and a right cardiac tricuspid annulus are independently and sequentially conducted while potential maps are formed. For this reason, it takes two to four hours or a maximum of six hours to conduct these tests. That is, such tests require a long period of time.

In addition, even after an accessory pathway portion is determined upon formation of a potential map, the ablation catheter is guided, under X-ray fluoroscopy, to a position where cauterization is to be performed, and an electrical stimulus is applied in the ventricle again, thereby conducting an electrophysiological test. Therefore, the test time is further prolonged. For this reason, a heavy burden is imposed on a patient, and a problem is posed in terms of exposure to X-rays.

SUMMARY OF THE INVENTION

The present invention has been in consideration of the above conventional methods, and has as its object to provide an accessory pathway detecting apparatus and method which can shorten the test time and reduce the burden on a patient.

It is another object of the present invention to provide an accessory pathway detecting apparatus which can simultaneously measure action potentials at multiple points and efficiently detect an accessory pathway.

It is still another object of the present invention to provide an accessory pathway detecting apparatus which displays action potentials measured at multiple points in the form of a list (e.g., a potential map) and allows an operator to easily recognize a conduction time of a stimulus at each point.

It is still another object of the present invention to provide an accessory pathway detecting apparatus which can simultaneously measure action potentials at multiple points on almost the entire circumference of a valve ring of the heart, and can easily detect an accessory pathway.

It is still another object of the present invention to provide an accessory pathway detecting apparatus which can detect an accessory pathway by means of impedance measurement.

It is still another object of the present invention to provide an accessory pathway detecting apparatus and an accessory pathway cauterizing apparatus in which an impedance measuring electrode is arranged on an accessory pathway ablation catheter to detect an accessory pathway by impedance measurement, thereby easily locating the ablation catheter at a portion to be cauterized.

It is still another object of the present invention to provide an accessory pathway cauterizing apparatus in which an ablation catheter having an impedance measuring electrode is inserted and located at a position near an accessory pathway portion recognized upon simultaneous measurement of action potentials at multiple points, and the final position of the abtation catheter can be determined by impedance measurement, thereby easily and quickly positioning the ablation catheter.

According to an arrangement of an accessory pathway detecting apparatus of the present invention for achieving the above objects, the apparatus includes a first electrode member which is inserted in a first detection portion of an object (to be tested) to measure a plurality of action potentials at the detection portion, and a second electrode member which is inserted in a second detection portion of the object to measure a plurality of action potentials at the portion, wherein action potential signals from the first and second electrode members are simultaneously measured at multiple points, and the obtained action potentials are output such that the action potentials can be displayed at once in the form of a list.

The output of the action potentials is preferably display of a list on a display means such as a CRT, or printing of a list by a printing unit.

According to another arrangement of the accessory pathway detecting apparatus of the present invention, the apparatus includes a first electrode member inserted in a first portion of an object to be tested and having a plurality of electrodes, a second electrode member inserted in a second portion of an object to be tested and having a plurality of electrodes, and an ablation catheter for cauterizing an accessory pathway portion, wherein the ablation catheter has an electrode for measuring an impedance between the electrode and each of the electrodes of the first and second electrode members.

It is preferable that the first electrode member have a plurality of independent electrodes to simultaneously obtain action potentials at multiple points, and the plurality of electrodes be at predetermined intervals from the distal end portion of the first electrode member in the direction of the proximal end portion. Note that the predetermined intervals may not be constant.

It is preferable that the second electrode member have a plurality of independent electrodes to simultaneously obtain action potentials at multiple points, and the plurality of electrodes be at predetermined intervals from the distal end portion of the second electrode member in the direction of the proximal end portion. In addition, the second electrode lead preferably has physical characteristics equivalent to those of a PTCA (percutaneous transluminal coronary angioplasty) guide wire in terms of wire diameter and elastic force.

The accessory pathway detecting apparatus preferably has a pacing means for giving an electrophysiological stimulus pulse into the object. In addition, the pacing means preferably has a pacing lead inserted in the object.

The pacing lead can be inserted into the inside of the heart through a vessel, and therefore, it can output the stimulus pulse from the inside of the heart.

It is preferable that the pacing lead have two or more electrodes and the direction of the distal end portion of the pacing lead can be controlled by a controller arranged at the proximal end portion of the pacing lead to be easily guided to a target portion.

In addition, the pacing means preferably gives a stimulus pulse by using the ablation catheter.

Furthermore, the accessory pathway detecting apparatus preferably has a bioelectric amplifier for amplifying intercardiac potential from each electrode lead.

Moreover, it is preferable that the bioelectric amplifier independently and simultaneously amplify a plurality of intercardiac potentials supplied from each electrode lead.

According to a procedure for an accessory pathway detecting method of the present invention, a first electrode member is inserted in a first portion of an object to be tested, and a second electrode is inserted in a second portion of the object. Action potential signals obtained by the first and second electrode members are measured at multiple points, and potential maps indicating the respective measured action potentials are output such that the potential maps can be simultaneously displayed in the form of a list. The impedance between an electrode near an accessory pathway portion, obtained in accordance with the potential maps, and an electrode arranged on the ablation catheter for cauterizing the accessory pathway portion is measured.

The potential maps are preferably stored in a memory upon conversion of the obtained signals into digital data and output to an output unit such that the data can be displayed in the form a list.

The output unit is preferably a CRT or a printing unit.

An output means for the measurement result of the impedance is preferably display of numeral values and acoustic output.

According to the above arrangement, the first electrode member is inserted in the coronary sinus to measure intercardiac potentials at mitral annulus, and the second electrode member is inserted in the right coronary artery to measure intercardiac potentials at the tricuspid annulus. A plurality of intercardiac potentials obtained by the respective electrode members are output as a potential map such that the intercardiac potentials can be displayed in the form of a list. A preexcitation portion obtained from the display can be detected as an accessory pathway portion.

According to another arrangement of the accessory pathway detecting apparatus of the present invention, the ablation catheter is inserted in a portion in the ventricle in which an accessory pathway is expected to be present, and the impedance between each of the electrodes of the first or second electrode member and the electrode of the ablation catheter is measured. A point where the lowest impedance is measured is detected as the accessory pathway portion, and the ablation catheter is fixed at the portion. With this operation, the ablation catheter can be easily fixed at the accessory pathway portion to cauterize this portion.

According to a procedure for an accessory pathway detecting method of the present invention, a first electrode member is inserted in the coronary sinus of the heart to measure intercardiac potentials at the mitral annulus, and a second electrode member is inserted in the right coronary artery of the heart to measure action potentials at the tricuspid annulus. A plurality of action potentials obtained by each electrode member are output as potential maps such that the intercardiac potentials can be displayed in the form of a list. The ablation catheter is inserted in the ventricle and located at a position near a preexcitation portion obtained from the display, and the impedance between each of the electrodes of the first or second electrode lead and the electrode of the ablation catheter is measured. A point where the lowest impedance is measured is detected as an accessory pathway portion, and the ablation catheter is fixed at the portion, thereby easily fixing the ablation catheter at the accessory pathway portion and cauterizing this portion.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specifications, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

(First Embodiment)

An accessory pathway detecting apparatus according to the first embodiment of the present invention will be described below with reference to FIGS. 1 to 5.

Figure 1:
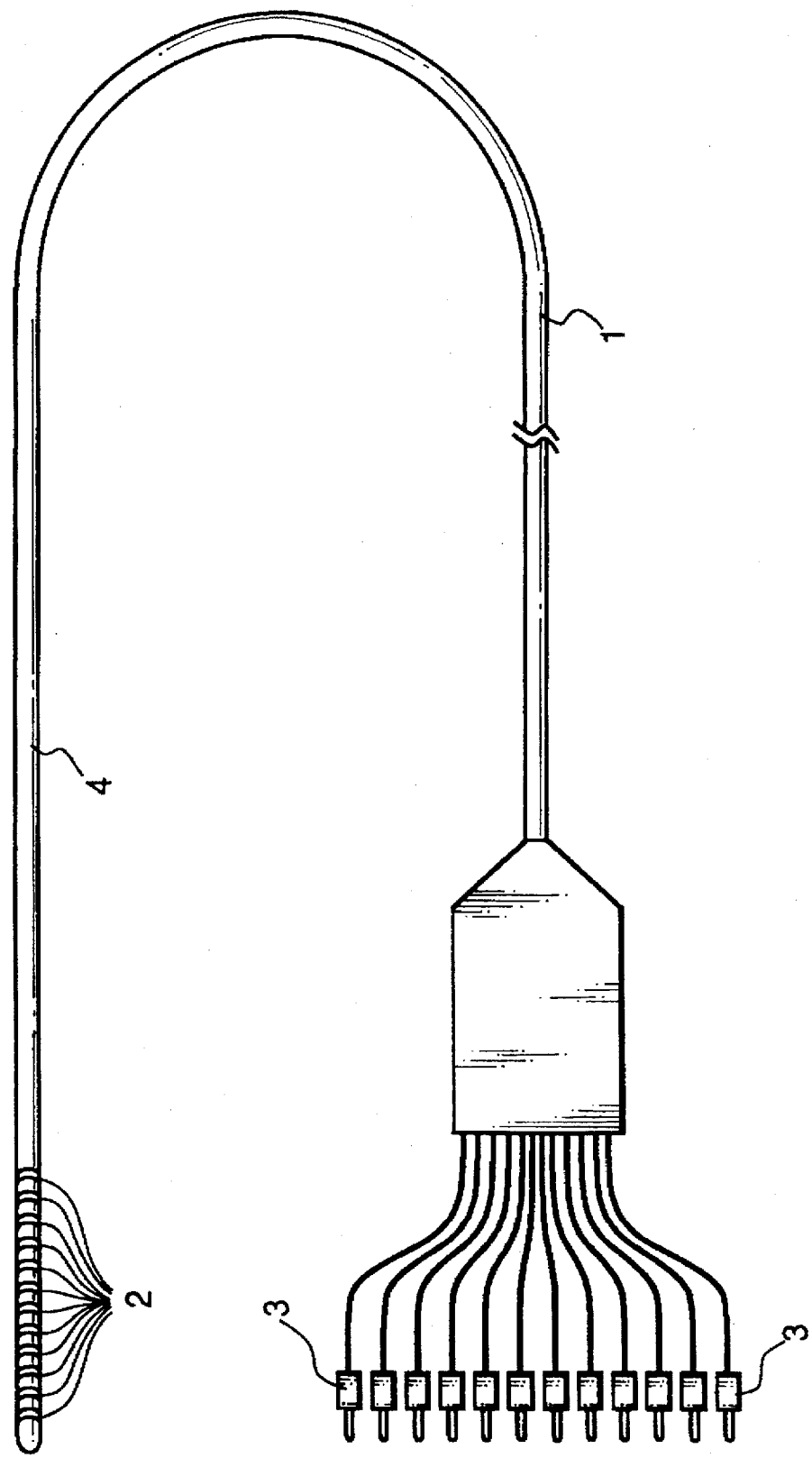
FIG. 1 is a view showing a left cardiac potential measuring multi-electrode lead according to an embodiment of the present invention.

FIG. 1 shows a left cardiac potential measuring multi-electrode lead 1 as a first electrode member, which is inserted through the coronary sinus to measure action potentials in the mitral annulus. Referring to FIG. 1, reference numeral 2 denotes a plurality (12 in this case) of electrodes mounted on the distal end of the left cardiac potential measuring multi-electrode lead 1; 3, signal extraction terminals mounted on the proximal end of the multi-electrode lead 1; and 4, a catheter tube 4 for guiding the electrodes 2 into the body. Referring to FIG. 1, the electrodes 2 are connected to the signal extraction terminals 3 via signal lines (not shown) which extend through the catheter tube 4 and are equal in number to the electrodes. Since the coronary sinus has a relatively large diameter, a multi-electrode lead of a catheter type like the one shown in FIG. 1 can be inserted in the coronary sinus.

Figure 2:
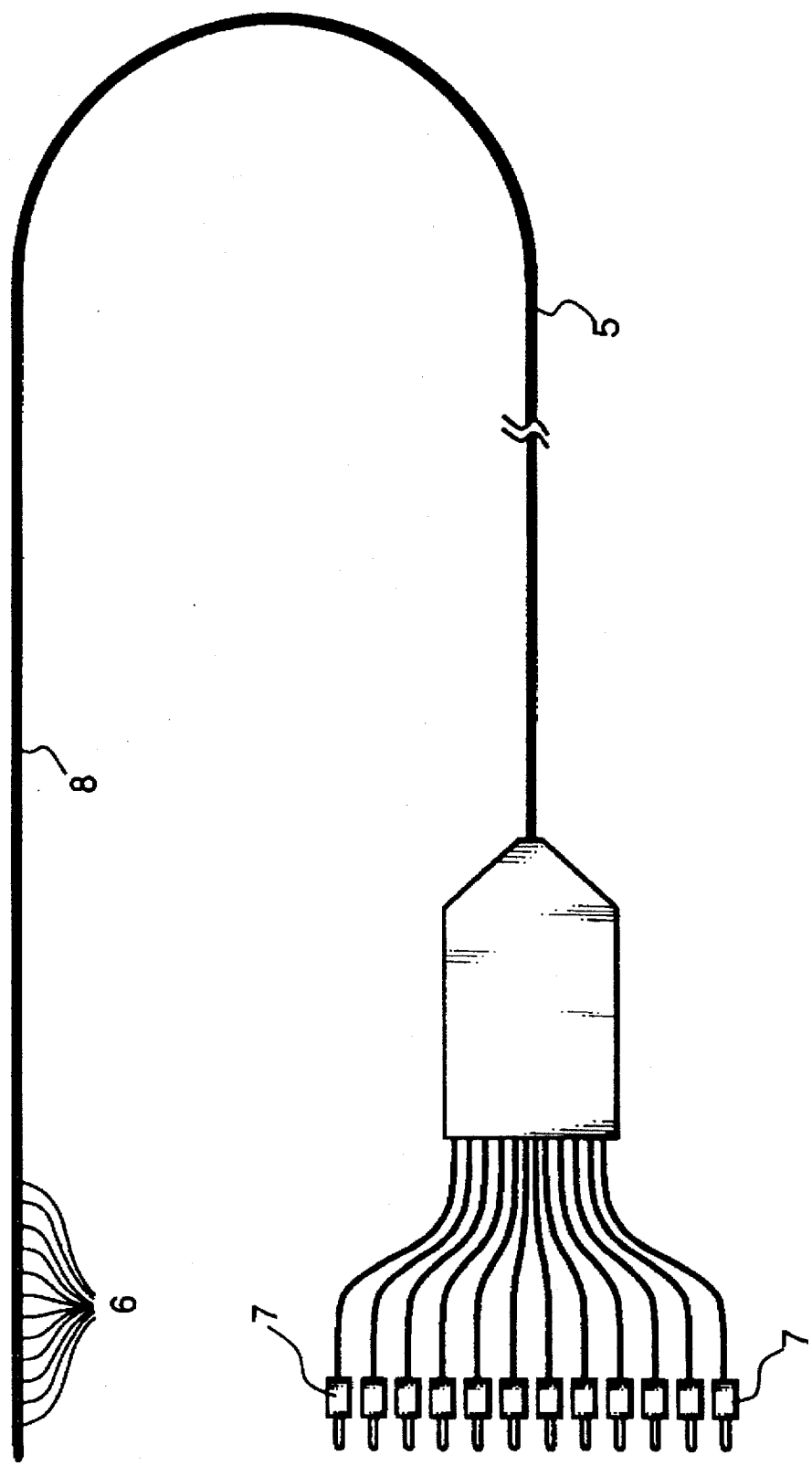
FIG. 2 is a view showing a right cardiac potential measuring multi-electrode lead according to the embodiment of the present invention.

FIG. 2 shows a right cardiac potential measuring multi-electrode lead 5 as a second electrode member, which is inserted into the right coronary artery to measure intercardiac potentials in the right cardiac tricuspid annulus. Referring to FIG. 2, reference numeral 6 denotes a plurality (12 in this case) of electrodes mounted on the distal end of the right cardiac potential measuring multi-electrode lead 5; 7, signal extraction terminals mounted on the proximal end of the multi-electrode lead 5; and 8, a guide wire for guiding the electrodes 6 into the body. Since the diameter of the right coronary artery is smaller than that of the coronary sinus, it is difficult to insert a multi-electrode lead of a catheter type like the one shown in FIG. 1 into the right coronary artery. For this reason, in order to insert a multi-electrode lead into the right coronary artery, the lead is preferably a multi-electrode lead of a guide wire type like the one shown in FIG. 2. In this case, a multi-electrode lead is formed by the following method. A plurality (12 in this case) of superfine signal lines, each coated with an insulating film in advance, are wound on the surface of a superelastic alloy wire in the form of a coil. Thereafter, portions of the insulating films of these signal lines are stripped off, at positions where the signal lines should serve as electrodes, in such a manner that the resultant electrodes are not in electrical contact with each other.

Figure 13:
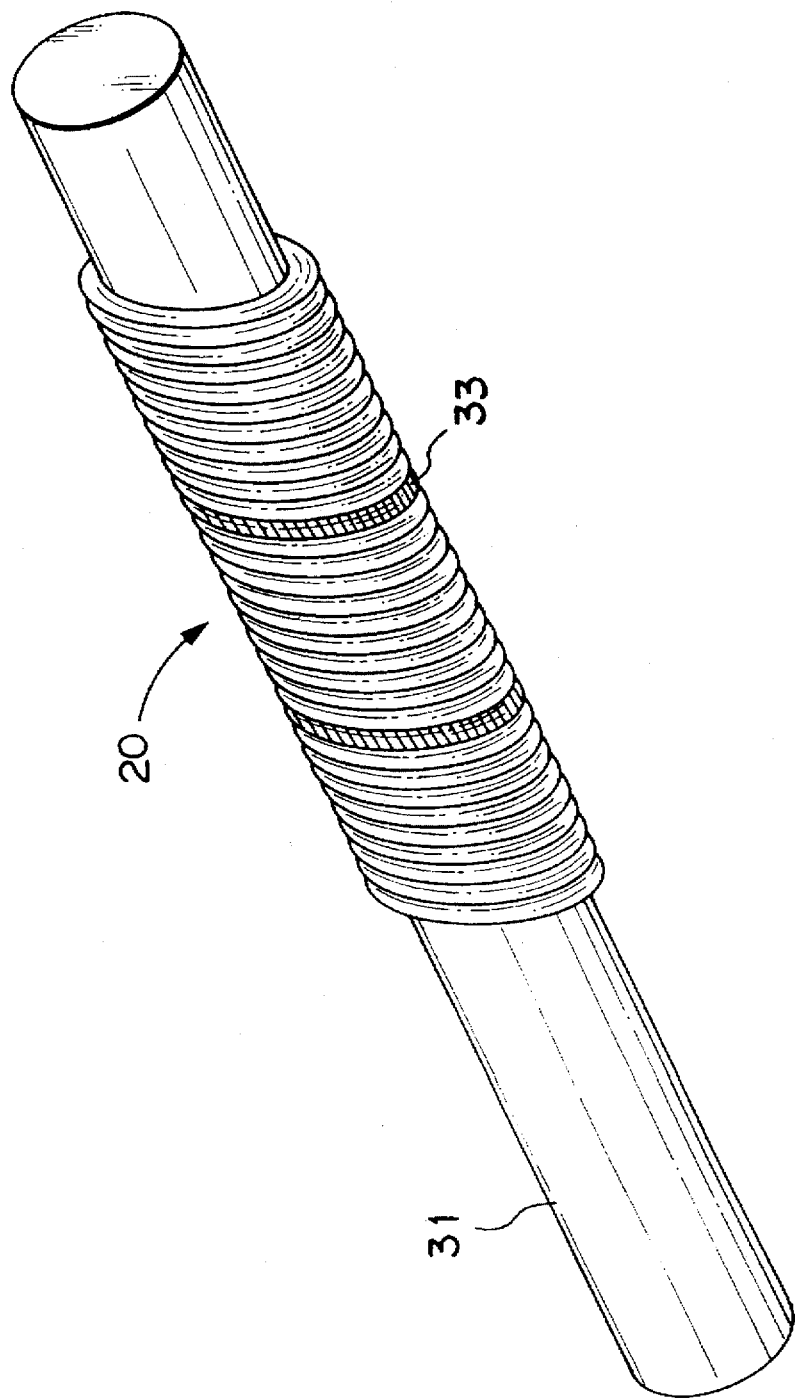
FIG. 13 is a perspective view for explaining the multi-electrode lead shown in FIG. 2.

With the superfine signal wire wound on the superelastic alloy wire 31 as described above, as shown in FIG. 13, the isolating coating of a portion of these twelve wires 20 is stripped by an amount of almost one circumference, exposing the gold-plating layer inside the isolating coating as indicated by reference numeral 33. Consequently, the conductive portion is exposed, and this exposed portion can be used as an intercardiac electrode.

By this method, a multi-electrode lead can be obtained, which has a diameter small enough to allow insertion of the lead into the right coronary artery and has electrodes large enough in number to conduct a test.

In this embodiment, the first and second leads 1 and 5 respectively have the 12 electrodes 2 and the 12 electrodes 6. If the number of electrodes of a multi-electrode lead of the catheter or guide wire type increases, the diameter of the multi-electrode lead itself increases, resulting in difficulty in inserting the multi-electrode lead into a vessel. In contrast to this, as the number of electrodes of the multi-electrode lead decreases, the precision of detection of an accessory pathway deteriorates. In this case, therefore, the number of electrodes is set to be 12 in consideration of the size of the heart and the distance between the electrodes.

Figure 3A:
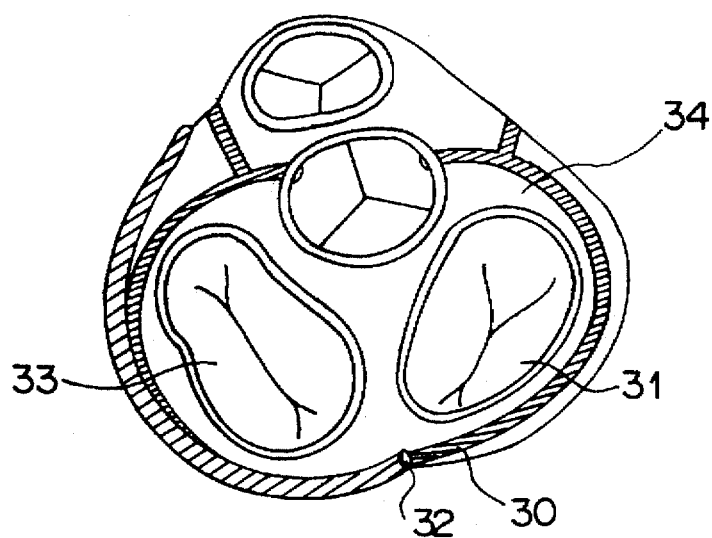
FIG. 3A is a sectional view of the atrium of the heart.
Figure 3B:
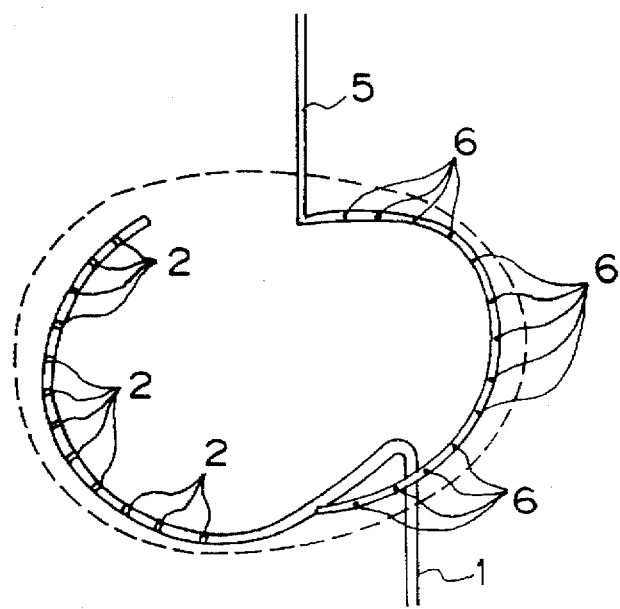
FIG. 3B is a perspective view showing a state wherein the left and right cardiac potential measuring multi-electrode leads according to the embodiment of the present invention are inserted in the heart.

FIGS. 3A and 3B are views for explaining the operating states of the first lead 1 for left cardiac potential measurement and the second electrode lead 5 for right cardiac potential measurement according to the embodiment.

FIG. 3A is a sectional view of the atrioventricular annulus. Reference numeral 30 denotes a right coronary artery in which the multi-electrode lead 5 is inserted; 31, a tricuspid valve, 32, a coronary sinus in which the multi-electrode lead 1 is inserted; 33, a mitral valve, and 34, an annulus.

FIG. 3B shows a state wherein both the first and second electrode leads 1 and 5 are respectively inserted into an artery and a vein in the heart. As shown in FIG. 3B, when the multi-electrode leads 1 and 5 are inserted into the coronary sinus and the right coronary artery, the electrodes 2 and 6 mounted on the distal ends of the multi-electrode leads are arranged around almost the entire circumferences of the annulus. Therefore, stimulus conduction times can be measured throughout almost the entire circumferences of the valve rings in which an accessory pathway exits.

Figure 4:
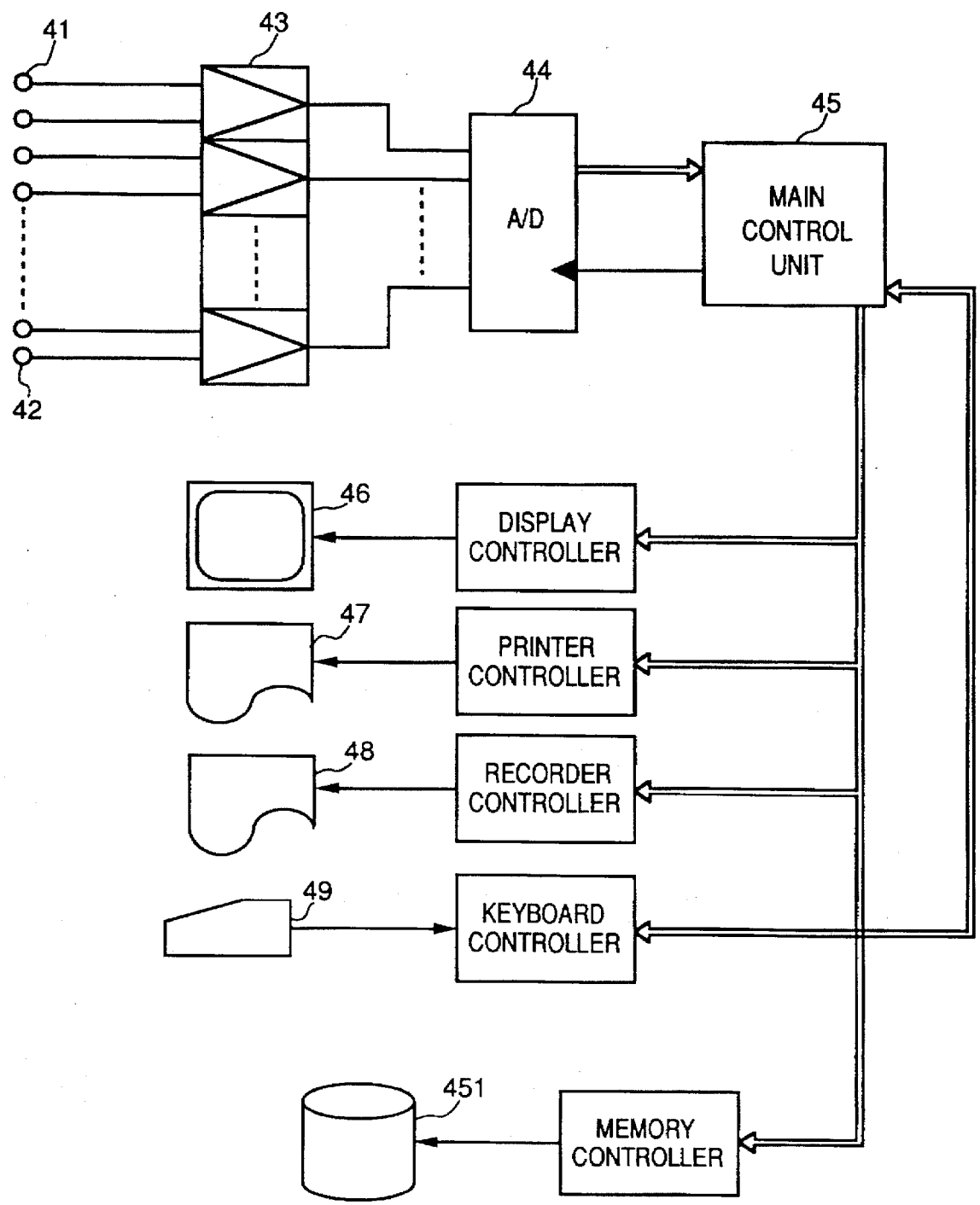
FIG. 4 is a block diagram showing an accessory pathway detecting apparatus according to the first embodiment of the present invention.

FIG. 4 is a block diagram showing the overall accessory pathway detecting apparatus of the first embodiment of the present invention. Reference numeral 41 denotes left cardiac connection terminals for connecting the multi-electrode lead 1; and 42, right cardiac connection terminals for connecting the multi-electrode lead 5. Although the numbers of terminals 41 and 42 are equal to those of the electrodes 2 and 6 in practice, most of them are omitted in FIG. 4 but are indicated by a dotted line. Reference numeral 43 denotes an amplifier for amplifying weak signals detected by the terminals 41 and 42; 44, an A/D converter for converting the analog signals obtained from the amplifier 43 into digital signals; and 45, a main control unit for storing these signals and performing control. Reference numeral 46 denotes a CRT as a display unit; 47, a printer as a printing unit; and 48, a recorder as a recording unit. These units can respectively display, print, and record supplied potential maps. Reference numeral 49 denotes an operation panel for externally operating this apparatus; and 451, a memory for storing measurement data used to form potential maps. The memory 451 may store image data for potential maps.

Figure 5:
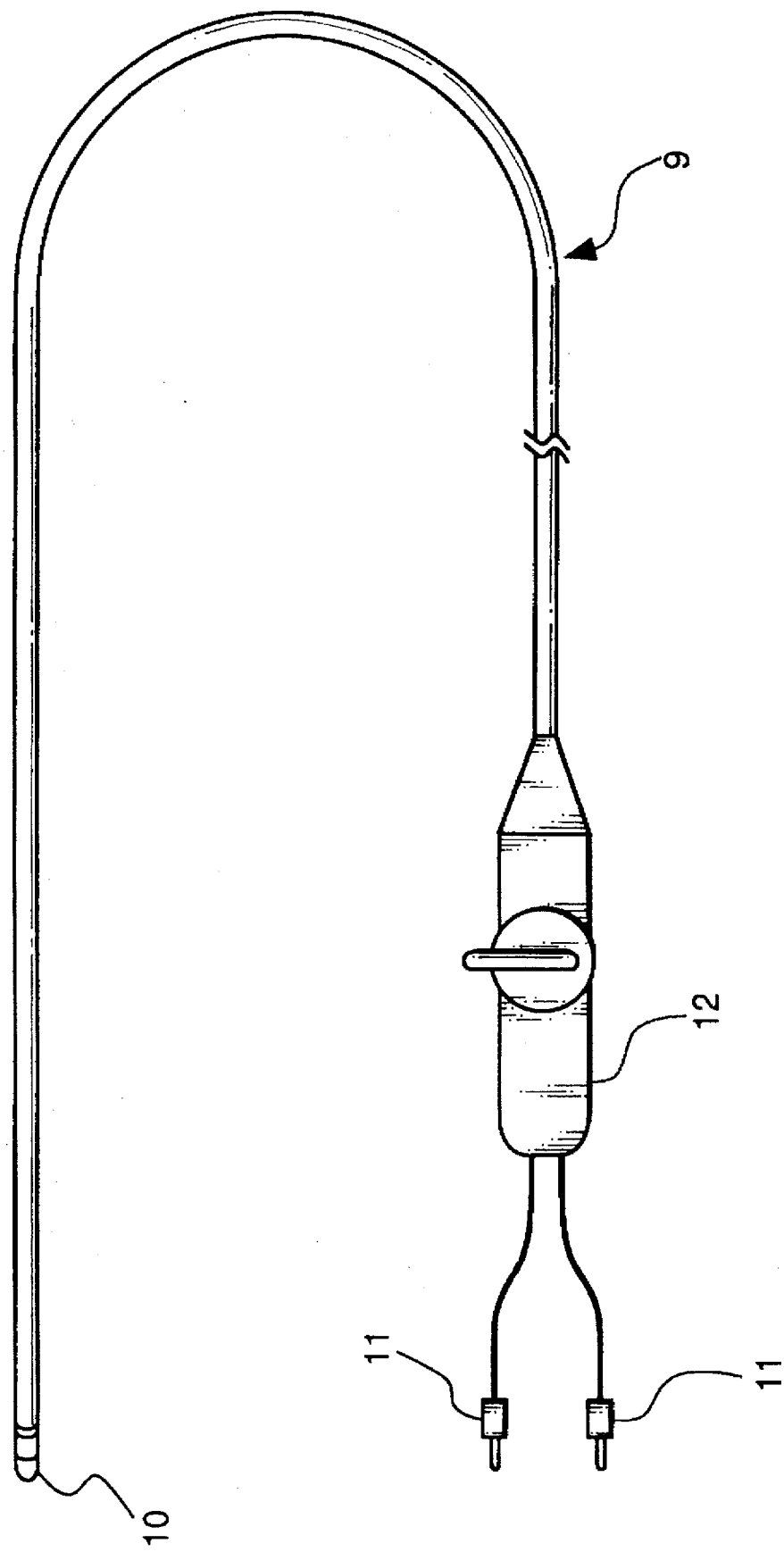
FIG. 5 is a view showing a pacing lead according to the first embodiment of the present invention.

FIG. 5 shows a pacing lead inserted into the atrium of the heart to give a stimulus to the heart. Referring to FIG. 5, reference numeral 9 denotes a pacing lead 9; 10, a distal end portion electrode 10 for generating a stimulus; 11, proximal end portion electrodes; and 12, steering for bending the distal end portion of the pacing lead 9 to facilitate insertion thereof into the body.

The distal end portion electrode 10 includes at least one positive electrode and one earth electrode.

Action potential signals are detected by the first and second electrode leads 1 and 5 inserted into the heart (object to be tested), as shown in FIG. 3B, and the signals at all the electrodes 24 are simultaneously loaded via the left cardiac connection terminals 41 and the right cardiac connection terminals 42. These signals are amplified by the amplifier 43 and converted into digital signal by the A/D converter 44. The digital signals are then sent to the main control unit 45. The main control unit 45 stores the obtained signals, and can output the signals altogether, as potential maps, to the CRT 46 or the printer 47 in accordance with a request generated by the operator through the operation panel 49. The 12 electrodes of each of the first and second electrode leads 1 and 5 are arranged at intervals of about 10 mm. During a test, the operator performs measurement, until an abnormal action potential appears, while observing a display of a potential map and gradually shifting each multi-electrode lead.

Figure 6:
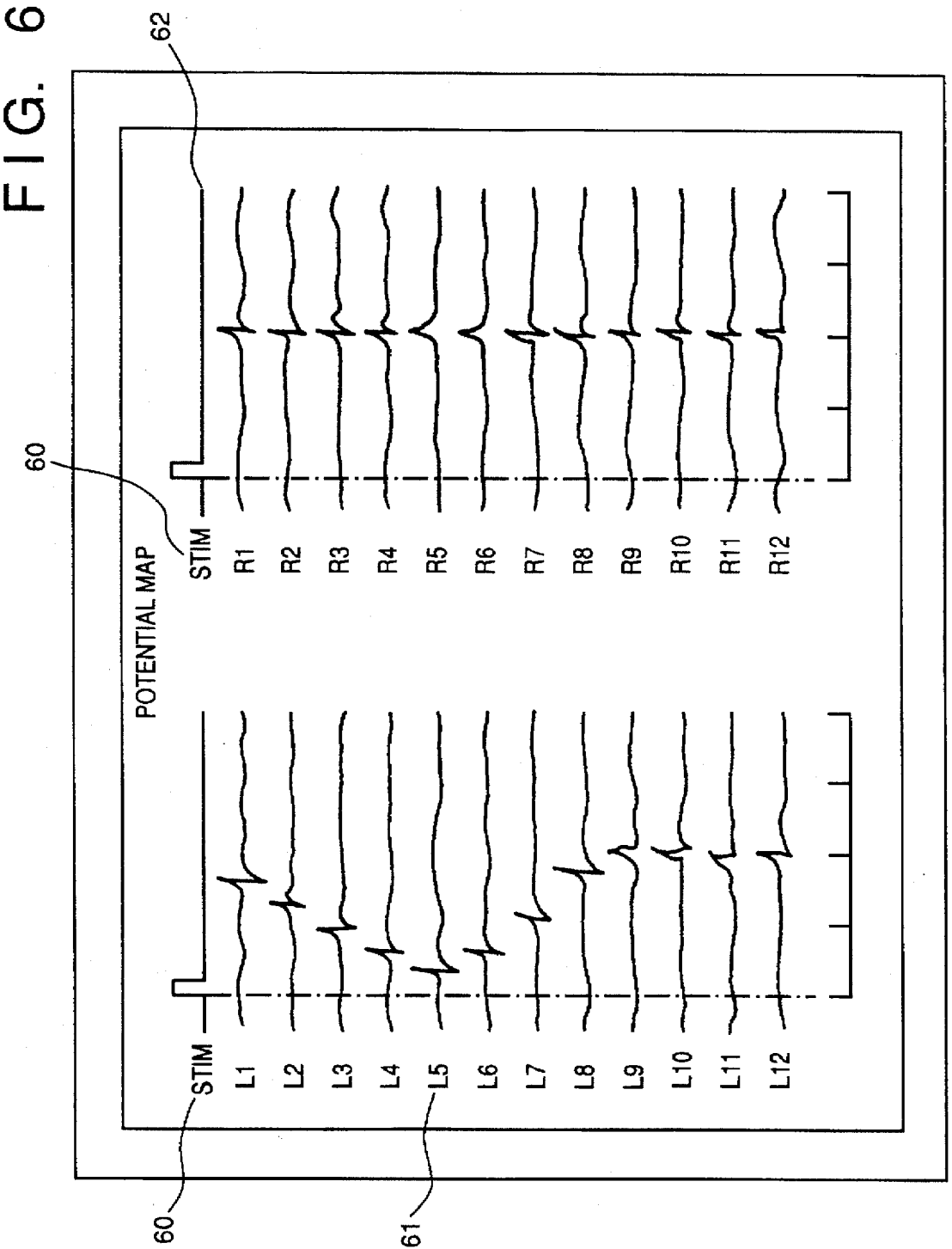
FIG. 6 is a view showing an output example of a potential map according to the first and third embodiments of the present invention.

FIG. 6 shows an output example of the potential maps. Reference numeral 60 denotes a time point at which a stimulus is given to the heart by the pacing lead 9. In this case, the start of display of the potential corresponds to the timing at which the stimuli are given to the heart. Reference numeral 61 denotes a case wherein action potentials, in the left cardiac mitral valve ring, measured by the 12 electrodes (L1 to L12) of the multi-electrode lead 1 are displayed; and 62, a case wherein action potentials, in the right cardiac tricuspid valve ring, measured by the 12 electrodes (R1 to R12) of the second electrode lead 5 are displayed. In each display, the axis of abscissa indicates time. That is, each display indicates how much time it takes for the stimulus given at the time point 60 to reach, as an action potential, to each of the electrodes (L1 to L12; R1 to R12) of the multi-electrode leads. In this case, as is apparent, conduction of the stimulus potential to the myocardium at the position of the electrode L5 of the multi-electrode lead 1 in the left cardiac mitral valve ring is too fast, i.e., abnormal. That is, it is apparent that an accessory pathway exists near the electrode L5.

Figure 10:
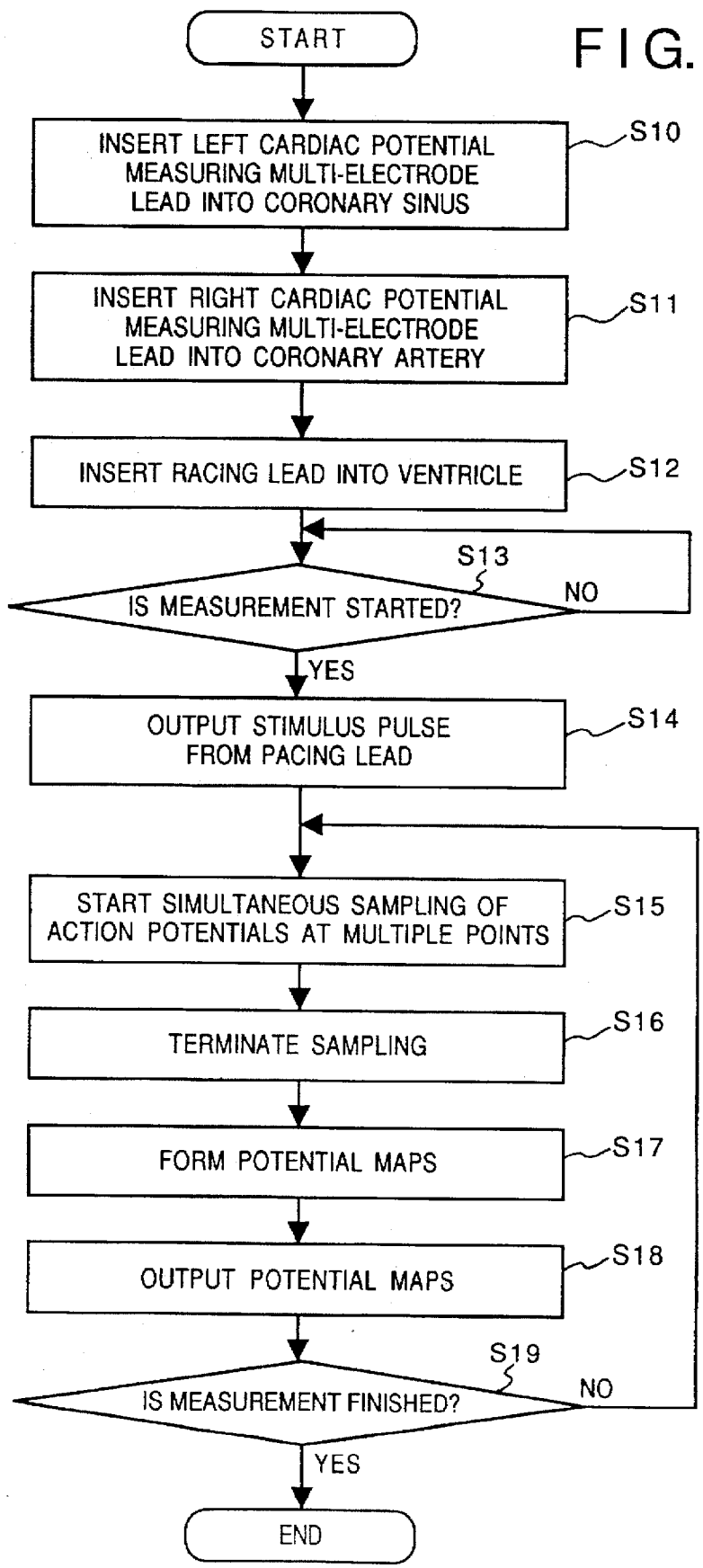
FIG. 10 is a flow chart showing a procedure for detecting an accessory pathway in the first embodiment.

FIG. 10 is a flow chart showing a procedure for detecting an accessory pathway in the first embodiment. In step S10, the left cardiac potential measuring multi-electrode lead 1 is inserted into the coronary sinus of an object to be tested, as shown in FIG. 3B. In step S11, the right cardiac potential measuring multi-electrode lead 5 is inserted in the coronary artery of the object, as shown in FIG. 3B. In addition, the pacing lead 9 is inserted into the ventricle of the object.

When measurement is started in the above state, the flow advances from step S13 to step S14. In step S14, a stimulus pulse is output from the distal end portion electrode 10 of the pacing lead 9. In step S15, action potentials detected by the respective electrodes 2 and 6 of the multi-electrode leads 1 and 5 are simultaneously sampled. The sampled data is stored in a RAM (not shown) incorporated in the main control unit 45. In this embodiment, the output timing of a stimulus pulse is transmitted from a power supply (not shown) for the pacing lead 9 to the main control unit 45, thereby establishing synchronization between output of a stimulus pulse and measurement of action potentials.

In step S16, sampling of potentials is terminated, and in step S17, potential maps are formed by using the sampled data stored in the RAM of the main control unit 45. In step S18, the image data of the obtained potential maps is output to a display controller 461, a controller 471, or a recorder controller 491. Each controller visually outputs the potential maps through the CRT 46, the printer 47, or the recorder 48, as shown in FIG. 6. The potential maps may be stored in the memory 451, floppy disk (not shown) or CD-ROM (not shown) or other memory devices.

The above described process indicated by steps S14 to S18 is repeated until the finish of the measurement is indicated.

As described above, an accessory pathway portion can be detected more accurately by repeating the accessory pathway detection processing in FIG. 10 while shifting the positions of the multi-electrode leads 1 and 5.

(Second Embodiment)

An accessory pathway detecting apparatus according to the second embodiment of the present invention will be described next with reference to FIGS. 7 to 8B.

Figure 7:
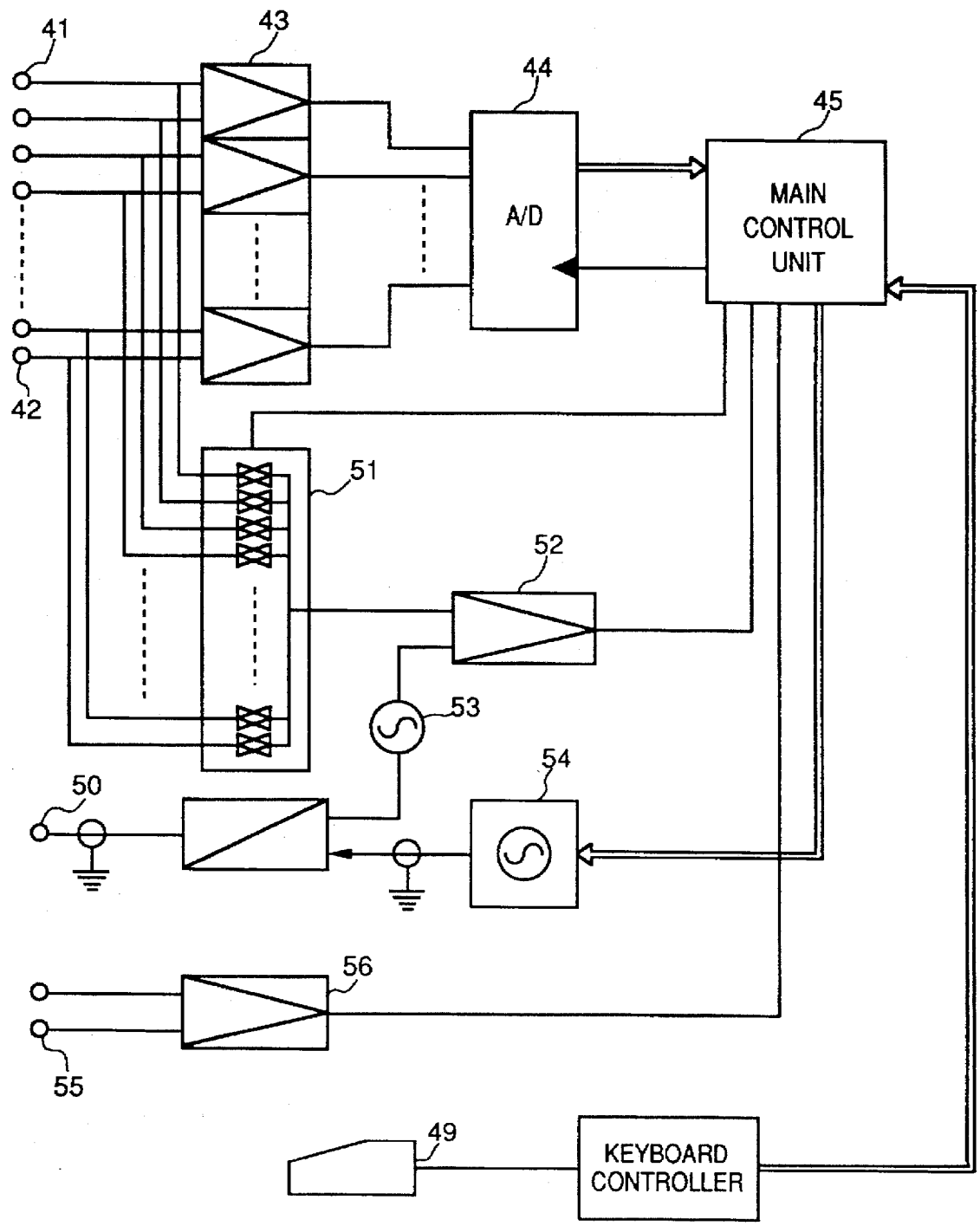
FIG. 7 is a block diagram showing an accessory pathway detecting apparatus according to the second embodiment of the present invention.

FIG. 7 is a block diagram showing the overall arrangement of the accessory pathway detecting apparatus of the second embodiment. Reference numeral 41 denotes left cardiac connection terminals for connecting the multi-electrode lead 1; and 42, right cardiac connection terminals for connecting the multi-electrode lead 5. Although the numbers of terminals 41 and 42 are equal to those of the electrodes 2 and 6 in practice, most of them are omitted in FIG. 4 but are indicated by a dotted line. Reference numeral 43 denotes an amplifier for amplifying weak signals detected by these terminals; 44, an A/D converter for converting the analog signals obtained from the amplifier 43 into digital signals; 45, a main control unit for storing these signals and performing control; 49, an operation panel for externally operating this apparatus; 50, an ablation catheter connection terminal 50; 51, a multiplexer for selecting one of a plurality of electrodes from the 24 electrodes of the first and second electrode leads; 52, an impedance measuring circuit 52 for measuring an impedance between an electrode selected by the multiplexer 51 and an electrode arranged in an ablation catheter; and 56, a temperature measuring circuit.

The same reference numerals in the accessory pathway detecting apparatus having the above arrangement denote the same parts as in the first embodiment shown in FIGS. 1 to 6, and only different points between the embodiments will be described below. The connection terminals 41 and 42 connected to the first and second electrode leads are connected to the multiplexer 51. The multiplexer 51 selects one (or a plurality of) electrode from the 24 electrodes in accordance with the operation of the operation panel 49, and connects the selected electrode (or electrodes) to the impedance measuring circuit 52. The impedance measuring circuit 52 is also connected to the impedance measuring electrode arranged in the ablation catheter via the connection terminal 50. The impedance measuring circuit 52 causes an impedance measuring power supply 53 to apply a voltage between the electrode of the ablation catheter and the electrode (or electrodes) selected by the multiplexer 51, and detects a current (or currents) generated between the electrodes. An accessory pathway portion is low in electrical impedance. Therefore, an accessory pathway is present at a position, between the electrodes of the first and second electrode leads and the electrode of the ablation catheter, at which the lowest impedance appears.

Figure 8A:
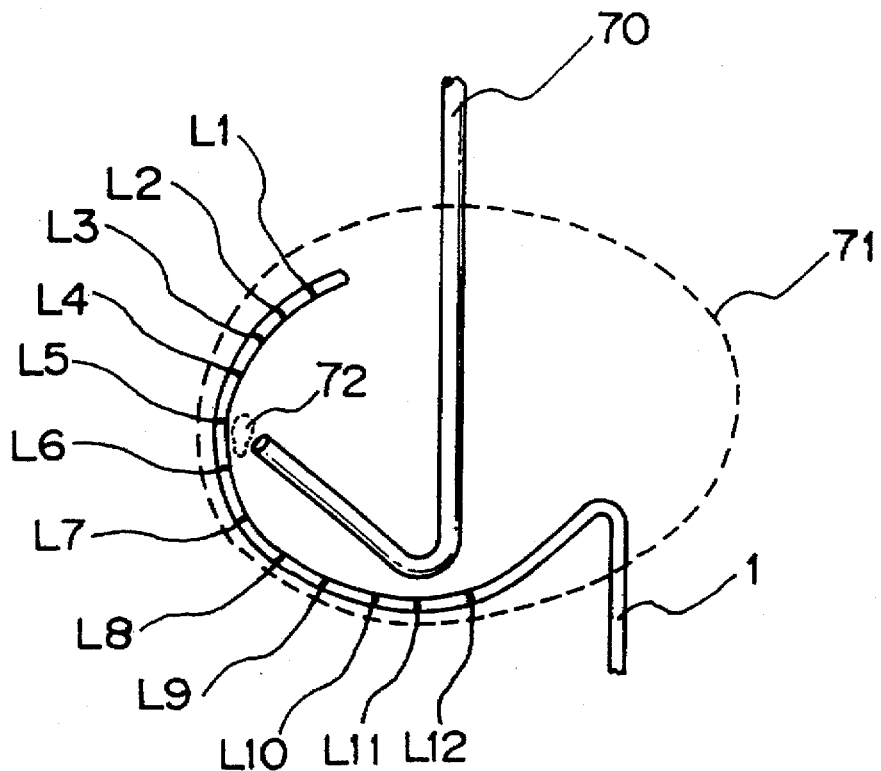
FIG. 8A is a perspective view showing a state wherein the left and right cardiac potential measuring multi-electrode leads according to the second and third embodiments of the present invention are inserted in the heart.
Figure 8B:
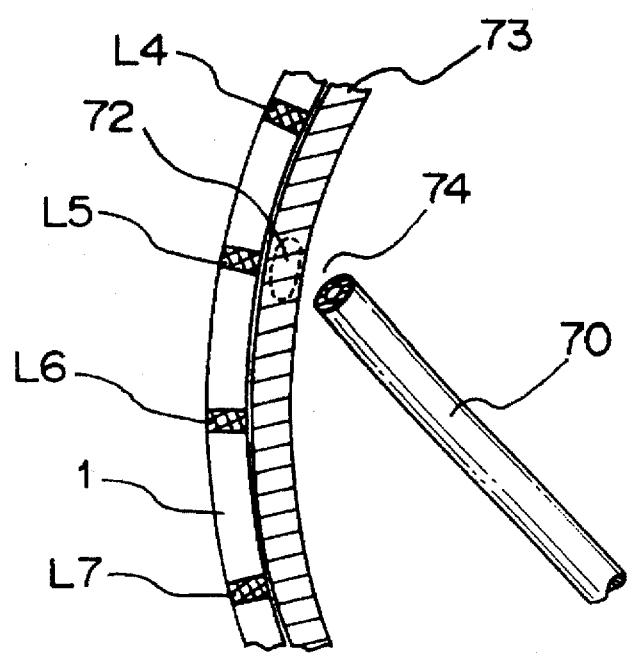
FIG. 8B is an enlarged view of a portion of FIG. 8A.

FIGS. 8A and 8B are views for explaining the operating states of the first electrode lead 1 for left cardiac potential measurement and the ablation catheter. Assume that an accessory pathway exists on the left cardiac side. In this case, therefore, illustration of the second electrode lead 5 is omitted.

Referring to FIG. 8A, reference numeral 70 denotes an ablation catheter; 71, an atrioventricular annulus 71 of the heart; and 72, an accessory pathway portion. Reference symbols L1 to L12 denote the electrodes of the first electrode lead 1.

Referring to FIG. 8B, reference numeral 73 denotes a cardiac muscular tissue; and 74, an ablation electrode also serving as an impedance measuring electrode.

As shown in FIG. 3B, the first and second electrode leads 1 and 5 are inserted into the heart (object to be tested). As shown in FIG. 8A, the distal end portion of the ablation catheter 70 is then moved to a position near the first and second electrode leads 1 and 2, thereby sequentially measuring impedances, starting from the electrode L1 of the first electrode lead 1. As described above, since an accessory pathway portion is lower in electrical impedance than the normal myocardium, a portion, between the electrodes of the first and second electrode leads and the electrode of the ablation catheter, which exhibits the lowest impedance can be specified as an accessory pathway. Therefore, an accessory pathway portion can be easily detected by measuring impedances in this manner. At the same time, the ablation catheter can be fixed at the corresponding position.

Assume, in this case, that an accessory pathway portion exists near the electrode L5 of the first electrode lead 1. As shown in FIG. 8B, since the accessory pathway portion 72 exists in the cardiac muscular tissue 73 near the electrode L5, the impedance between the electrode L5 and the impedance measuring electrode 74 is lower than that of each of the remaining electrodes (L1 to L4; L6 to L12) of the first electrode lead 1 and the impedance measuring electrode 74. In addition, since the impedance decreases as the ablation catheter 70 approaches the electrode L5, the position of the accessory pathway portion 72 can be specified. When the position of the accessory pathway portion 72 is specified, the ablation electrode at the distal end of the ablation catheter is fixed to the accessory pathway portion 72. After the ablation electrode is fixed, energy such as microwaves or RF current is irradiated from the ablation electrode onto the accessory pathway portion, thereby cauterizing the accessory pathway portion.

If cauterization is performed at an excessively high temperature, a portion other than the accessory pathway portion may be damaged. In contrast to this, if cauterization is performed at an excessively low temperature, the accessory pathway portion may not be completely cauterized to be left. For this reason, the resistance of a temperature measuring thermistor mounted on the distal end of the ablation catheter 70 is detected by the temperature measuring circuit 56 to be output as a temperature value.

A procedure for cauterizing an accessory pathway portion in the second embodiment will be described in detail next with reference to the flow chart shown in FIG. 11.

Figure 11:
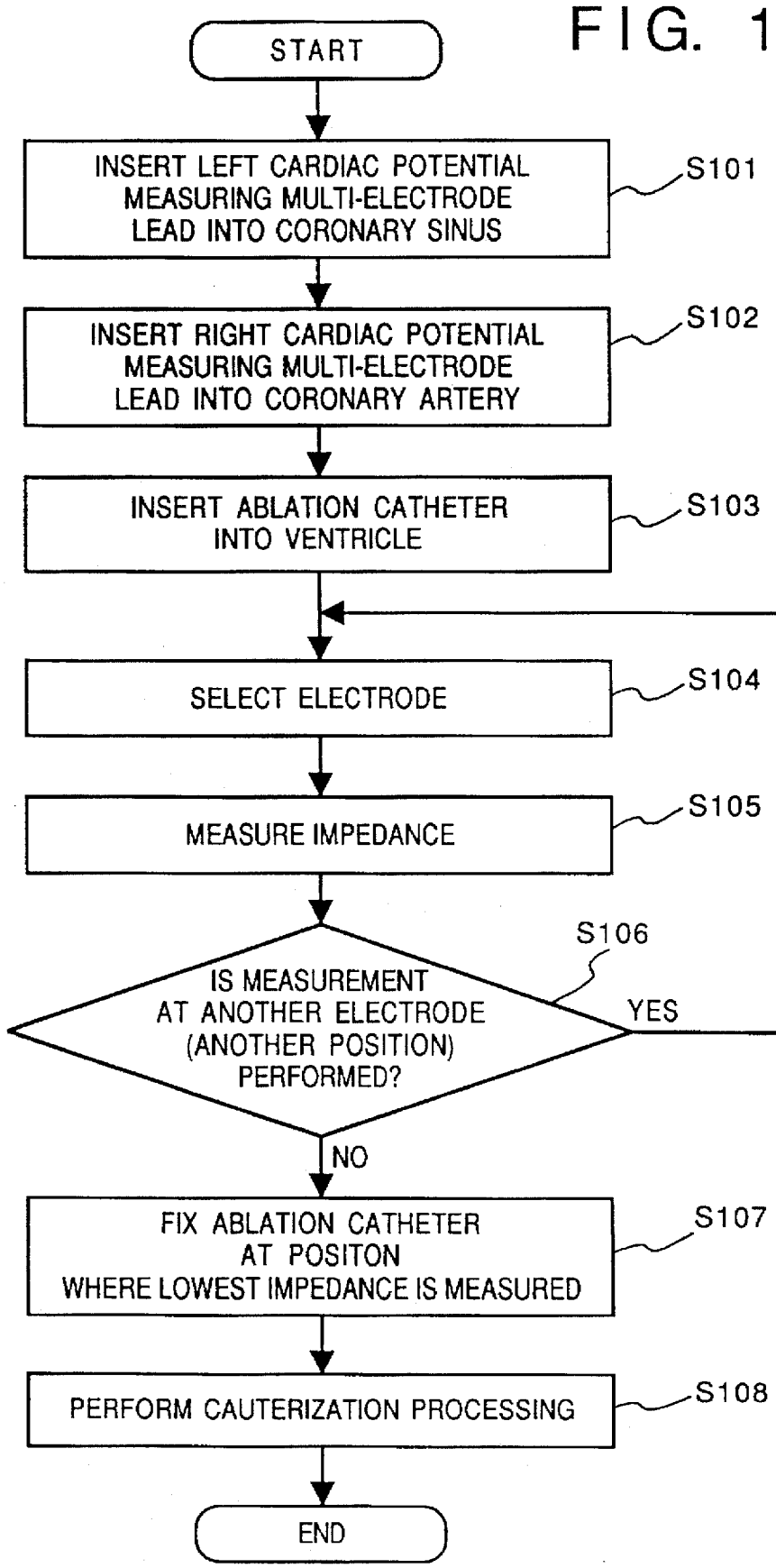
FIG. 11 is a flow chart showing a procedure for cauterizing an accessory pathway portion in the second embodiment.

FIG. 11 is a flow chart for explaining the procedure for cauterizing an accessory pathway portion in the second embodiment. First of all, the multi-electrode leads are inserted into predetermined portions (steps S101 and S102), similar to steps S10 and S11 in the first embodiment. In step S103, the ablation catheter 70 is inserted into the ventricle of the object. In this case, the ablation catheter 70 has the ablation electrode 74, which also serves as the impedance measuring electrode, at its distal end portion. In addition, the ablation catheter 70 has a temperature sensor. A signal from the sensor is input to the temperature measuring circuit 56 via a terminal 55.

In step S104, the multiplexer 51 selects an electrode used for impedance measurement from the electrodes of the multi-electrode leads 1 and 5. The selected electrode is connected to the impedance measuring circuit 52 via the multiplexer 51. In step S105, impedance measurement is performed. More specifically, a predetermined AC voltage is generated by the impedance measuring power supply 53, and a current flowing through an electrode 73 of the catheter and the selected one of the electrodes of the multi-electrode leads is detected, thereby obtaining an impedance.

When impedance measurement is to be performed with respect to another electrode of the multi-electrode leads, the flow returns to step S104 to cause the multiplexer 51 to select an electrode so as to repeat impedance measurement. Alternatively, impedance measurement may be repeated by moving the catheter 70 without changing selection of an electrode.

When impedance measurement is completed, the catheter 70 is fixed at a position where the lowest impedance is detected, and cauterization processing is executed (step S108). Cauterization processing is performed by emitting energy, supplied from an ablation power supply 54, via the ablation electrode 74. In the cauterization processing, a signal from the temperature sensor of the ablation catheter 70 is input to the temperature measuring circuit 56 via the terminal 55. The temperature measuring circuit 56 converts the signal into temperature data and inputs the data to the main control unit 45. The main control unit 45 properly controls the output of the cauterization power supply 54 while monitoring the temperature in ablation.

Note that the position where the catheter is to be fixed can be efficiently obtained by detecting an electrode near an accessory pathway portion in advance by using a potential map like the one in the first embodiment, and locating the catheter at a position near the detected electrode upon insertion in step S103.

As is apparent, similar to the first embodiment (FIG. 4), this embodiment may also include a memory 451 for storing a potential map.

(Third Embodiment)

An accessory pathway detecting method and apparatus according to the third embodiment of the present invention will be described next with reference to FIG. 9.

Figure 9:
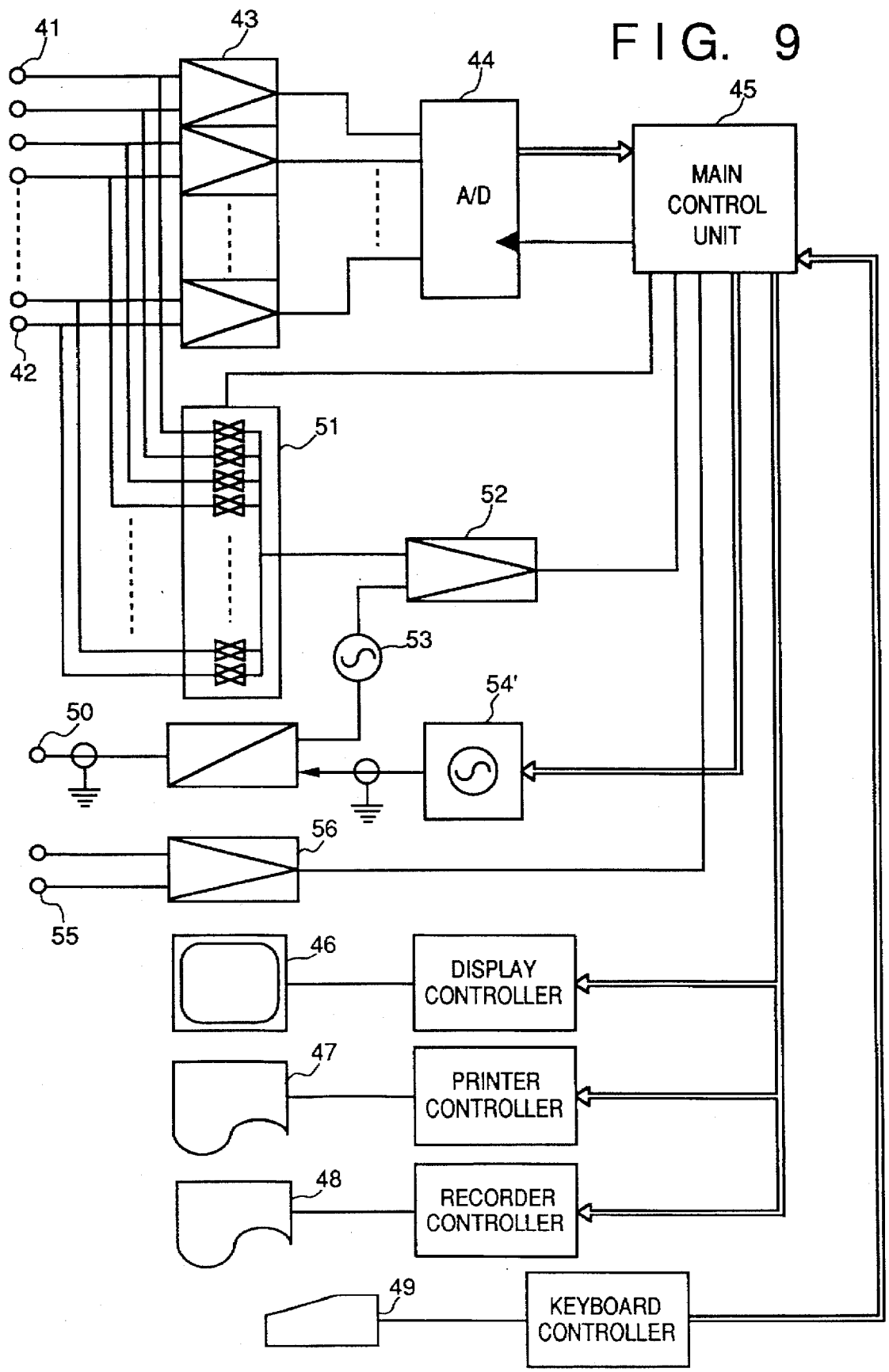
FIG. 9 is a block diagram showing an accessory pathway detecting apparatus according to the third embodiment of the present invention.

FIG. 9 is a block diagram showing the overall arrangement of an apparatus used for an accessory pathway detecting method according to the third embodiment of the present invention. Reference numeral 41 denotes left cardiac connection terminals for connecting the first electrode lead 1 in FIG. 1; and 42, right cardiac connection terminals for connecting the multi-electrode lead 5 in FIG. 2. Although the numbers of terminals 41 and 42 are equal to those of the electrodes 2 and 6 in practice, most of them are omitted in FIG. 9 but are indicated by a dotted line. Reference numeral 43 denotes an amplifier for amplifying weak signals detected by these terminals; 44, an A/D converter for converting the analog signals obtained from the amplifier 43 into digital signals; and 45, a main control unit for storing these signals and performing control. Reference numeral 46 denotes a CRT; 47, a printer; and 48, a recorder. These components can respectively display, print, and store the obtained potential maps. Reference numeral 49 denotes an operation panel for externally operating this apparatus; 50, an ablation catheter connection terminal 50; 51, a multiplexer for selecting one of a plurality of electrodes from the 24 electrodes of the first and second electrode leads; 52, an impedance measuring circuit 52 for measuring an impedance between an electrode selected by the multiplexer 51 and an electrode arranged in an ablation catheter; 55, thermistor lead terminals connected to a thermistor for measuring the temperature of the distal end of the ablation catheter in cauterization processing; and 56, a temperature measuring circuit for converting a signal obtained by the thermistor into a temperature value.

The same reference numerals in the accessory pathway detecting apparatus having the above arrangement denote the same parts as in the first and second embodiments shown in FIGS. 1 to 8, and a description thereof will be omitted.

The first and second electrode leads 1 and 2 inserted in the heart (object to be tested) in the manner shown in FIG. 3A detect action potential signals appearing upon application of a stimulus given by an ablation catheter 70 also having the function of a pacing lead and inserted in the ventricle. The main control unit 45 outputs the action potential signals altogether, as potential maps, to the CRT 46 or the printer 47. With these potential maps, the operator can run through the action potential signals detected by the 24 electrodes of the first and second electrode leads 1 and 2. When, as shown in FIG. 6, the operator knows that an accessory pathway portion is present near the electrode L5 of the multi-electrode lead 1, he/she brings the ablation catheter 70 close to the electrode L5 and specifies the accurate position of the electrode L5 by measuring the impedance between the electrode L5 and an impedance measuring electrode 74 of the ablation catheter 70.

In this case, the operator generally moves the ablation catheter 70 while observing an X-ray image. If, therefore, impedance values are displayed as numerical values or presented by another visual means, the operator needs to grasp two types of visual information at once, resulting in a complicated operation. For this reason, the magnitude of an impedance is presented as the pitch of a sound to allow the operator to concentrate on the X-ray image and operate the ablation catheter 70.

When the accurate position of the accessory pathway portion is determined in this manner, the ablation catheter 70 is fixed in the same manner as described above in the second embodiment, and the accessory pathway portion is cauterized.

If ablation is performed at an excessively high temperature, a portion other than the accessory pathway portion may be damaged. In contrast to this, if ablation is performed at an excessively low temperature, the accessory pathway portion may be completely cauterized. For this reason, the resistance of a temperature measuring thermistor mounted on the distal end of the ablation catheter 70 is detected by the temperature measuring circuit 56 to be output as a temperature value.

In order to confirm that an accessory pathway portion is completely cauterized after cauterization, an electrophysiological test is preferably performed again to output a potential map. According to the third embodiment, since the ablation catheter 70 also has the function of a pacing lead, the electrophysiological test can be conducted without inserting an instrument again.

Figure 12:
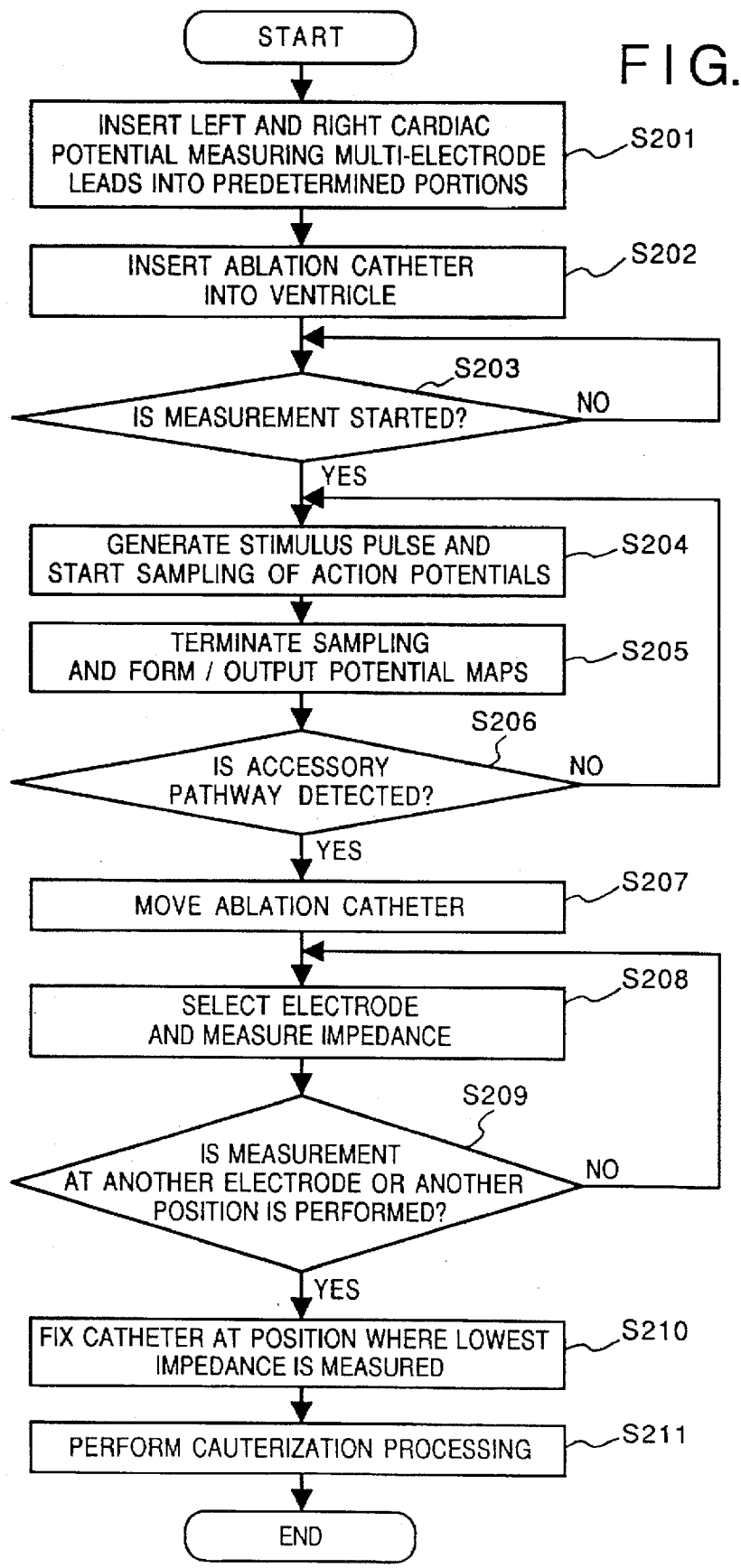
FIG. 12 is a flow chart showing a procedure for cauterizing an accessory pathway portion in the third embodiment.

A procedure for detection and cauterization of an accessory pathway in the third embodiment will be described below. FIG. 12 is a flow chart showing the procedure for detection and cauterization of an accessory pathway in the third embodiment.

The left and right cardiac potential measuring multi-electrode leads 1 and 5 are respectively inserted into predetermined portions (step S201). The ablation catheter is inserted into the ventricle (step S202). The above processing is performed according to the same procedure for the processing in steps S101 to S103 in the second embodiment. In this case, the electrode 74 of the ablation catheter 70 also serves as an electrode for outputting an electrical stimulus pulse, an impedance measuring electrode, and an ablation electrode. Therefore, a power supply 54' serves as both a power supply for ablation and a power supply for an electrical stimulus pulse.

When action potential measurement is started, a stimulus pulse is output from the ablation catheter, and sampling of action potentials is started. When measurement is executed for a predetermined period of time, a potential map is formed from the sampled data, and the potential map is output (steps S203 to S205). The above processing is the same as that in steps S13 to S18 described above.

From the obtained potential map, one of the electrodes of the multi-electrode leads 1 and 5 is identified as an electrode near an accessory pathway portion, and the ablation catheter is moved to a position near the electrode (steps S206 to S207).

If the accessory pathway is not detected, the steps S204 and S205 are repeated.

Subsequently, the electrode near the accessory pathway portion is selected, and an impedance is measured. The ablation catheter is fixed at a position where the lowest impedance is measured, and cauterization processing is performed (steps S208 to S211). The above processing is the same as that in steps S104 to S108.

A multi-electrode lead of a guide wire type shown in FIG. 2 may be used as the first electrode member which is inserted through the coronary sinus.

As has been described above, according to the present invention, since an accessory pathway portion can be easily specified within a short period of time, the burden on a patient, especially the possibility of exposure to X-rays, can be reduced. In addition, since the ablation catheter can be easily fixed, the burden on the patient can be further reduced.

As many apparently widely different embodiments of the present invention can be made without departing from the spirit and scope thereof, it is to be understood that the invention is not limited to the specific embodiments thereof except as defined in the claims.

What is claimed is:

1. An accessory pathway detecting apparatus for detecting an accessory pathway in an object to be tested, comprising:

a first electrode member having a plurality of electrodes located along a longitudinal extent of the first electrode member, said first electrode member having a wire shape capable of being inserted in a coronary sinus to acquire action potentials at a plurality of locations along the coronary sinus;

a second electrode member having a plurality of electrodes located along a longitudinal extent of said second electrode member, said second electrode member having a wire-like shape capable of being inserted in a coronary artery to acquire action potentials at a plurality of locations along the coronary artery;

measuring means for simultaneously measuring the action potentials at the plurality of locations by using said first and second electrode members; and output means for visually outputting measurement results obtained by said measuring means.

2. The apparatus according to claim 1, wherein said output means outputs data displayed on a display on the basis of the measurement results.

3. The apparatus according to claim 1, wherein said output means outputs data printed on a recording medium by a printing unit on the basis of the measurement results.

4. The apparatus according to claim 1, wherein said output means stores data based on the measurement results in a data storage media.

5. The apparatus according to claim 1, wherein the plurality of electrodes of each of said first and second electrode members are insulated from each other and arranged at predetermined intervals on a distal end portion of each of said first and second electrode members.

6. The apparatus according to claim 1, wherein said first electrode member is in a shape of a catheter.

7. The apparatus according to claim 1, wherein said second electrode member is in a shape of a guide wire.

8. The apparatus according to claim 1, wherein said second electrode member is in a shape of a guide wire and has physical characteristics equivalent to those of a PTCA guide wire in terms of at least wire diameter and elastic force.

9. The apparatus according to claim 1, wherein said first electrode member has a diameter small enough to allow said member to be inserted in a coronary sinus, and said second electrode member has a diameter small enough to allow said member to be inserted in a coronary artery.

10. The apparatus according to claim 1, further comprising pacing means for giving an electrical stimulus to the object.

11. The apparatus according to claim 10, wherein said pacing means is adapted to be inserted in a predetermined portion in the object to give the object a stimulus pulse for an electrophysiological test.

12. The apparatus according to claim 10, wherein the measurement results obtained by said measuring means indicate a conduction time taken to conduct an electrical stimulus given by said pacing means to each electrode of said first and second electrode members.

13. An accessory pathway detecting apparatus for detecting an accessory pathway in an object to be tested, comprising:

a first electrode member having a plurality of electrodes insulated from each other and having a shape capable of being inserted in the object;

action potential measuring means for simultaneously measuring action potentials at a plurality of locations by using the plurality of electrodes of said first electrode member;

a second electrode member having a shape capable of being inserted in the object and having an electrode at a predetermined position; and measuring means for measuring an impedance between each electrode of said first electrode member and the electrode of said second electrode member.

14. The apparatus according to claim 13, wherein said first electrode member is in a shape of a wire, and the plurality of electrodes on said first electrode member are arranged at predetermined intervals on a distal end portion of said first electrode member.

15. The apparatus according to claim 13, wherein said measuring means comprises:

selecting means for selecting at least one of the plurality of electrodes of said first electrode member, applying means for applying a predetermined voltage between the selected electrode and the electrode of said second electrode member, and detecting means for detecting a current generated on the basis of the applied voltage, wherein an impedance is acquired on the basis of the predetermined voltage and the current detected by said detecting means.

16. The apparatus according to claim 15, further comprising notification means for performing notification on the basis of an impedance value obtained by said measuring means.

17. The apparatus according to claim 16, wherein said notification means notifies an impedance measured by said measuring means by means of a sound.

18. The apparatus according to claim 13, wherein said second electrode member is constituted by an ablation catheter.

19. An accessory pathway cauterizing apparatus for detecting and cauterizing an accessory pathway in an object to be tested, comprising:

a first electrode having a shape capable of being inserted in a first portion of the object and having a plurality of electrodes insulated from each other;

a second electrode having a shape capable of being inserted in a second portion of the object and having a plurality of electrodes insulated from each other;

action potential measuring means for simultaneously measuring action potentials at a plurality of locations by using the plurality of electrodes of said first and second electrode members;

an ablation catheter having an electrode arranged at a predetermined position; and measuring means for measuring an impedance between each electrode of said first and second electrode members and the electrode of said ablation catheter.

20. The apparatus according to claim 19, wherein each of said first and second electrode members is in a shape of a wire, and the plurality of electrodes insulated from each other and used to acquire a plurality of action potentials are arranged at predetermined intervals at a distal end portion of each of said electrode members.

21. The apparatus according to claim 20, wherein said first electrode member is in a shape of a catheter.

22. The apparatus according to claim 20, wherein said second electrode member is in a shape of a guide wire.

23. The apparatus according to claim 20, wherein said second electrode member is in a shape of a guide wire and has physical characteristics equivalent to those of a PTCA guide wire in terms of at least wire diameter and elastic force.

24. The apparatus according to claim 20, wherein said first electrode member has a diameter small enough to allow said member to be inserted in a coronary sinus, and said second electrode member has a diameter small enough to allow said member to be inserted in a coronary artery.

25. The apparatus according to claim 19, wherein the electrode of said ablation catheter is arranged on a distal end portion of said ablation catheter.

26. The apparatus according to claim 19, wherein said measuring means comprises selecting means for selecting at least one of the plurality of electrodes of said first electrode member, applying means for applying a predetermined voltage between the selected electrode and the electrode of said ablation catheter, and detecting means for detecting a current generated on the basis of the applied voltage, wherein an impedance is acquired on the basis of the predetermined voltage and the current detected by said detecting means.

27. The apparatus according to claim 26, further comprising notification means for performing notification on the basis of an impedance value obtained by said measuring means.

28. The apparatus according to claim 27, wherein said notification means notifies an impedance measured by said measuring means by means of a sound.

29. An accessory pathway detecting apparatus for detecting an accessory pathway in a heart to be tested, comprising:

a first electrode member having a plurality of electrodes located along a longitudinal extent of said first electrode member and insulated from each other, said first electrode member being in a shape of a wire and being capable of being inserted in a coronary sinus of the heart;

a second electrode member having a plurality of electrodes located along a longitudinal extent of the second electrode member and insulated from each other, said second electrode member being in the shape of a wire and being capable of being inserted in a coronary artery of the heart;

a third electrode member having a shape capable of being inserted in the heart and having an electrode at a predetermined position;

first measuring means for simultaneously measuring action potentials at a plurality of locations by using said first and second electrode members;

output means for visually outputting results obtained by said first measuring means; and second measuring means for measuring an impedance between each of the electrodes of said first and second electrode members and the electrode of said third electrode member.

30. An accessory pathway detecting apparatus for detecting and cauterizing an accessory pathway in an object to be tested, comprising:

a first electrode member having a plurality of electrodes located along a longitudinal extent of the first electrode member and insulated from each other, said first electrode member being in a shape of a wire and being capable of being inserted in a coronary sinus of the heart;

a second electrode member having a plurality of electrodes located along a longitudinal extent of the second electrode member and insulated from each other, said second electrode member being in a shape of a wire and being capable of being inserted in a coronary artery of the heart;

an ablation catheter having a shape capable of being inserted in the heart and having an electrode at a predetermined position;

first measuring means for simultaneously measuring action potentials at pluralities of locations by using said first and second electrode members;

output means for visually outputting results obtained by said first measuring means such that the results are displayed in the form of a list; and second measuring means for measuring an impedance between each of the electrodes of said first and second electrode members and the electrode of said ablation catheter.

31. The apparatus according to claim 30, wherein said ablation catheter has an electrode for generating an electrical stimulus, and the measurement results obtained by said first measuring means indicate a conduction time taken to conduct an electrical stimulus generated by said ablation catheter to a position of each electrode of said first and second electrode members.

32. The method of detecting an accessory pathway in an object to be tested, comprising the steps of:

inserting a first electrode member in a coronary sinus of a heart, said first electrode member being in a shape of a wire and having a plurality of electrodes located along a longitudinal extent of the first electrode member, said first electrode member being adapted to acquire action potentials at a plurality of locations along the coronary sinus;

inserting a second electrode member in a coronary artery of the heart, said second electrode member having a wire shape and a plurality of electrodes located along a longitudinal extent of the second electrode member, said second electrode member being adapted to acquire action potentials at a plurality of locations along the coronary artery;

simultaneously measuring the action potentials at the plurality of locations by using said first and second electrode members; and visually outputting measurement results obtained in said measuring step.

33. The method according to claim 32, further comprising the step of inserting a third electrode member in the heart, said third electrode member having an electrode for giving an electrical stimulus to the object.

34. A method of detecting an accessory pathway in an object to be tested, comprising the steps of:

inserting a first electrode member in the object, said first electrode member having a plurality of electrodes insulated from each other;

simultaneously measuring action potentials at a plurality of locations by using the plurality of electrodes of said first electrode member;

inserting a second electrode member in the object; said second electrode member having an electrode at a predetermined position; and measuring an impedance between each of the electrodes of said first electrode member and the electrode of said second electrode member.

35. A method of detecting and cauterizing an accessory pathway in an object to be tested, comprising the steps of:

inserting a first electrode member in a first portion of the object, said first electrode member having a plurality of electrodes insulated from each other;

inserting a second electrode member in a second portion of the object, said second electrode member having a plurality of electrodes insulated from each other;

simultaneously measuring action potentials at a plurality of locations by using the plurality of electrodes of said first and second electrode members;

inserting an ablation catheter having an electrode arranged at a predetermined position into the object and measuring an impedance between each of the electrodes of said first and second electrode members and the electrode of said ablation catheter; and specifying an accessory pathway portion on the basis of measurement results of the impedances, and cauterizing the accessory pathway portion by using said ablation catheter.

36. The method according to claim 35, wherein the first portion is a coronary sinus, and the second portion is a coronary artery.

37. A method of detecting an accessory pathway in an object to be tested, comprising the steps of:

inserting a first electrode member in a coronary sinus of a heart, said first electrode member having a wire shape and a plurality of electrodes located along a longitudinal extent of the first electrode member and insulated from each other;

inserting a second electrode member in a coronary artery of the heart, said second electrode member having a wire shape and a plurality of electrodes located along a longitudinal extent of the second electrode member and insulated from each other;

simultaneously measuring action potentials at a plurality of locations of the coronary sinus and coronary artery by using said first and second electrode members;

visually outputting measurement results obtained in said measuring step so that an accessory pathway portion can be recognized by the output;

inserting a third electrode member having an electrode into the heart to a position near the recognized accessory pathway portion; and specifying the accessory pathway portion by measuring an impedance between an electrode, of the electrodes of said first and second electrode members, located near the recognized accessory pathway portion and the electrode of said third electrode member.

38. A method of detecting and cauterizing an accessory pathway in an object to be tested, comprising the steps of:

inserting a first electrode member in a coronary sinus of a heart, said first electrode member having a wire shape and a plurality of electrodes located along a longitudinal extent of the first electrode member and insulated from each other;

inserting a second electrode member in a coronary artery of the heart, said second electrode member having a wire shape and plurality of electrodes located along a longitudinal extent of the second electrode member and insulated from each other;

simultaneously measuring action potentials at a plurality of locations along the coronary sinus and coronary artery by using said first and second electrode members;

visually outputting measurement results so that an accessory pathway portion in the heart can be recognized on the basis of the output;

inserting and locating an ablation catheter at the accessory pathway portion, said ablation catheter having an electrode at a predetermined position;

measuring an impedance between each of the electrodes of said first and second electrode members and the electrode of said ablation catheter, thereby detecting the accessory pathway portion accurately and fixing said ablation catheter; and cauterizing the accessory pathway portion by using said ablation catheter.

39. A method of detecting and cauterizing an accessory pathway in an object to be tested, comprising the steps of:

inserting a first electrode member in a coronary sinus of a heart, said first electrode member having a wire shape and a plurality of electrodes located along a longitudinal extent of the first electrode member and insulated from each other;

inserting a second electrode member in a coronary artery of the heart, said second electrode member having a wire shape and a plurality of electrodes located along a longitudinal extent of the second electrode member and insulated from each other;

inserting an ablation catheter in the heart, said ablation catheter having an electrode for generating a stimulus pulse and performing impedance measurement;

measuring a conduction time of a stimulus pulse generated by said catheter by simultaneously measuring action potentials at a plurality of locations along the coronary artery and the coronary sinus by using said first and second electrode members;

visually outputting measurement results so that an accessory pathway portion of the heart can be recognized on the basis of the output;

moving said ablation catheter to the accessory pathway portion of the heart;

measuring an impedance between each of the electrodes of said first and second electrode members and the electrode of said ablation catheter, thereby detecting the accessory pathway portion accurately and fixing said ablation catheter; and cauterizing the accessory pathway portion by using said ablation catheter.

* * * * *

UNITED STATES PATENT AND TRADEMARK OFFICE
CERTIFICATE OF CORRECTION

PATENT NO. : 5,741,214
DATED : April 21, 1998
INVENTOR(S) : Teruhiko OUCHI et al It is certified that error appears in the above-identified patent and that said Letters Patent is hereby corrected as shown below:

In Column 2, line 33, delete "abtation" and insert -- ablation --.
In Column 12, line 47, delete "wire-like" and insert -- wire --.

Signed and Sealed this

Twenty-eighth Day of July, 1998

Attest:

BRUCE LEHMAN

Attesting Officer

Commissioner of Patents and Trademarks